(12) United States Patent
Kochinke (10) Patent No.: US 11,052,055 B2
(45) Date of Patent: Jul. 6, 2021

(54) MODULAR TRANSDERMAL DELIVERY SYSTEM AND ASSOCIATED METHODS OF MANUFACTURE AND USE

(71) Applicant: International Bioceutical Co. LLC, San Diego, CA (US)

(72) Inventor: Frank Kochinke, San Jose, CA (US)

(73) Assignee: PURE RATIOS HOLDING, INC, San Diego, CA (US)

( * ) Notice: Subject to any disclaimer, the term of this patent is extended or adjusted under 35 U.S.C. 154(b) by 0 days.

(21) Appl. No.: 16/591,548

(22) Filed: Oct. 2, 2019

(65) Prior Publication Data
US 2020/0146998 A1 May 14, 2020

Related U.S. Application Data

(63) Continuation of application No. 16/013,856, filed on Jun. 20, 2018, now abandoned, which is a (Continued)

(51) Int. Cl.
*A61K 31/05* (2006.01)
*A61M 37/00* (2006.01)
(Continued)

(52) U.S. Cl.
CPC ........ *A61K 9/7084* (2013.01); *A61F 13/0279* (2013.01); *A61K 9/7038* (2013.01); (Continued)

(58) Field of Classification Search
CPC ......... A61F 13/0279; A61F 2013/0296; A61K 31/05; A61K 9/7038; A61K 9/7084; A61L 15/16; A61L 15/58; A61M 37/00
See application file for complete search history.

(56) References Cited

U.S. PATENT DOCUMENTS

| 3,797,494 A | 3/1974 | Zaffaroni |
| 4,911,916 A | 3/1990 | Cleary |
(Continued)

FOREIGN PATENT DOCUMENTS

| DE | 202011108434 U1 * | 1/2012 | .......... A61K 9/7084 |
| WO | 2005025549 A2 | 3/2005 | |
| WO | 2012/069820 A1 | 5/2012 | |

OTHER PUBLICATIONS

US 5,837,530 A, 10/1998, Reed, Jr. (withdrawn)
(Continued)

*Primary Examiner* — Ernst V Arnold
(74) *Attorney, Agent, or Firm* — Dianne E. Reed; VLP Law Group, LLP (57) ABSTRACT

A modular transdermal drug delivery system is provided, the system including: an upper module in which an outer backing layer is laminated to a pressure-sensitive adhesive layer that is covered by a removable release liner prior to assembly; and a lower module with a porous drug reservoir layer laminated to a skin-contact adhesive that affixes the system to the skin during drug delivery, where the skin-contact adhesive is, in one embodiment, an adhesive layer that is substantially co-extensive with the porous drug reservoir layer and, prior to use, protected with a second removable release liner. Methods of manufacture and use are also provided, as is an assembled transdermal drug delivery system fabricated by affixing the pressure-sensitive adhesive layer of the upper module to the porous drug reservoir layer of the lower module.

24 Claims, 3 Drawing Sheets

Related U.S. Application Data continuation of application No. 16/063,812, filed as application No. PCT/US2017/069125 on Dec. 29, 2017.

(60) Provisional application No. 62/440,149, filed on Dec. 29, 2016.

(51) Int. Cl.
 *A61K 9/70* (2006.01)
 *A61F 13/02* (2006.01)

(52) U.S. Cl.
 CPC ............ *A61K 31/05* (2013.01); *A61M 37/00* (2013.01); *A61F 2013/0296* (2013.01); *A61M 2205/123* (2013.01); *A61M 2207/00* (2013.01); *A61M 2209/088* (2013.01)

(56) References Cited

U.S. PATENT DOCUMENTS

| | | |
|---|---|---|
| 4,983,395 A | 1/1991 | Chang et al. |
| 5,217,718 A | 6/1993 | Colley et al. |
| 5,350,581 A | 9/1994 | Kochinke |
| 5,443,505 A * | 8/1995 | Wong ............... A61K 9/0051 623/4.1 |
| 5,591,123 A * | 1/1997 | Sibalis ............... A61M 37/00 604/20 |
| 5,613,958 A | 3/1997 | Kochinke et al. |
| 5,902,603 A | 5/1999 | Chen et al. |
| 6,159,497 A | 12/2000 | Laprade et al. |
| 7,175,853 B1 | 2/2007 | Bracht |
| 8,343,538 B2 | 1/2013 | Kanios et al. |
| 8,696,637 B2 | 4/2014 | Ross |
| 9,492,650 B2 | 11/2016 | Krinke |
| 2002/0111377 A1 | 8/2002 | Stinchcomb |
| 2005/0129749 A1 | 6/2005 | Strauss |
| 2005/0266061 A1 | 12/2005 | Stinchcomb et al. |
| 2005/0266085 A1 | 12/2005 | Warner et al. |
| 2006/0024358 A1 | 2/2006 | Santini et al. |
| 2008/0113013 A1 | 5/2008 | Koch |
| 2014/0243764 A1 | 8/2014 | Kanios et al. |
| 2014/0271940 A1 | 9/2014 | Wurzer |
| 2014/0335207 A1 | 11/2014 | Minton et al. |

OTHER PUBLICATIONS

English translation of DE-202011108434U1 2012; 6 pages. (Year: 2012).*

PCT Search Report and Written Opinion PCT/US2017/069125, dated Mar. 1, 2018.

"Extended Search Report, European Patent Application 17888554.7", dated Jun. 23, 2020, 7 pages.

Stanley, Christopher P., et al., "Is the cardiovascular system a therapeutic target for cannabidiol?", British Journal of Clinical Pharmacology 75(2), 2012, 313-322.

* cited by examiner

MODULAR TRANSDERMAL DELIVERY SYSTEM AND ASSOCIATED METHODS OF MANUFACTURE AND USE

CROSS-REFERENCE TO RELATED APPLICATIONS

This is a continuation of U.S. Ser. No. 16/013,856, filed Jun. 20, 2018, which was a continuation of Ser. No. 16/063,812, which claimed priority to International Patent Application No. PCT/US17/069125, filed Dec. 29, 2017, which in turn claimed priority to provisional U.S. Ser. No. 62/440,149, filed Dec. 29, 2016. The aforementioned patent applications are incorporated by reference in their entireties.

TECHNICAL FIELD

The invention relates generally to a modular transdermal delivery system. The invention additionally relates to a method for manufacturing the system and to a method for using the system in the transdermal delivery of a pharmacologically active agent. The invention has utility in the fields of medicine, drug delivery, and medical device manufacture.

BACKGROUND

The delivery of drugs through the skin provides many advantages; primarily, such a means of delivery is a comfortable, convenient and noninvasive way of administering drugs. The variable rates of absorption and metabolism encountered in oral treatment are avoided, and other inherent inconveniences—e.g., gastro-intestinal irritation and the like—are eliminated as well. Transdermal drug delivery also makes possible a high degree of control over blood concentrations of any particular drug.

Current transdermal drug delivery systems are, however, limited in several respects.

For instance, the active agent to be delivered through the skin is normally incorporated into the transdermal system as manufactured, limiting the system to delivery of that particular active agent; substitution of a different active agent by a downstream entity, e.g., by hospital personnel, is not possible.

As another example, a physician or other medical practitioner may determine, either prior to or during the drug delivery period, that a particular patient requires a modification in the dosage regimen. However, conventional transdermal systems do not allow for such modifications, e.g., a change in daily or total drug dosage, an increase or decrease in delivery rate, and/or a shortened or prolonged delivery period.

Additionally, current transdermal products are not reusable, in whole or in part, nor are they refillable. This limits the utility of transdermal systems, insofar as each system is for one-time use only and then disposed of. The potential lifetime of the manufacturing materials and compositions is cut short, and large-scale disposal of used transdermal drug delivery systems is potentially problematic from an environmental standpoint.

An ideal transdermal drug delivery system that would provide significant advantages relative to known transdermal systems would do some or all of the following:

Allow for modular manufacture, with post-manufacture drug loading and system assembly;

Be capable of delivering two or more different active agents, simultaneously or sequentially;

Enable delivery of two or more different active agent formulations containing the same active agent, where the formulations differ in concentration, inactive formulation components, or other properties;

Provide post-manufacture personnel (nurses, physicians, other hospital personnel, the user) with post-manufacture options with respect to active agent, dosage, release rate, and delivery period; and Be reusable in whole or in part.

Of potential interest to the present invention are the following:

U.S. Pat. No. 5,350,581 to Kochinke, which describes fabrication of a multilayer transdermal drug delivery system using a modular manufacturing system; U.S. Pat. No. 5,730,721 to Hyatt et al., which describes storage of a drug formulation and a carrier formulation in two separate envelopes, with a transdermal patch prepared by bringing the separate envelopes together;

U.S. Pat. No. 5,827,530 to Reed, Jr., describing a transdermal patch that is intended to be filled with an active agent after manufacture and assembly of a transdermal drug delivery system, where a drug formulation is injected into a fillable reservoir through a septum in a loading port;

U.S. Pat. No. 5,919,477 to Bevan et al., which pertains to a transdermal patch containing two or more active agents, with one active agent per reservoir in a laminated structure;

U.S. Pat. No. 8,784,874 to Strauss, which describes a laminated transdermal drug delivery system for administration of more than one active agent, with the active agents maintained in separate layer assemblies that are brought together post-manufacture;

U.S. Pat. Nos. 9,198,877 and 9,205,062 to Jackson et al., which provides a laminated transdermal drug delivery system in which each of a plurality of adhesive drug reservoirs provides a different drug delivery profile; and International Patent Publication No. WO 2012/069820 to Chowdhury, which describes a laminated transdermal patch in which the layers are manufactured and stored separately, in order to preclude premature drug release and minimize layer-layer incompatibility, where the layers are brought together to assemble the laminated system at the point of use.

SUMMARY OF THE INVENTION

Accordingly, the invention is directed to the aforementioned need in the art, and provides a modular transdermal delivery system for pre-use assembly and drug loading.

In one embodiment, the modular transdermal delivery system includes the following elements:

an upper module comprising an outer backing layer, a pressure-sensitive adhesive layer laminated thereto, and a first removable release liner covering the pressure-sensitive adhesive layer; and a lower module comprising a porous drug reservoir layer for adhering to the pressure-sensitive adhesive layer of the upper module upon assembly and into which a pharmaceutical formulation will be loaded, and a skin-contact adhesive affixed to the drug reservoir layer, wherein the system is drug-free but may be readily loaded with a pharmacologically active agent or active agent formulation prior to use.

Assembly of the system is carried out by loading an active agent formulation into the drug reservoir layer, removing the first release liner, aligning the upper module with the lower module, and bringing the two modules together so that the exposed pressure-sensitive adhesive layer of the upper module contacts and adheres to the upper surface of the lower module.

Thus, in another embodiment, the modular transdermal delivery system includes the following elements:

an upper module comprising an outer backing layer, a pressure-sensitive adhesive layer laminated thereto, and a first removable release liner covering the pressure-sensitive adhesive layer; and a lower module comprising a porous drug reservoir layer for adhering to the pressure-sensitive adhesive layer of the upper module upon assembly, a skin-contact adhesive affixed to the drug reservoir layer, and, contained within the porous drug reservoir layer, a formulation containing a pharmacologically active agent or a precursor thereto.

In both of the above embodiments, a second removable release liner preferably covers the exposed skin-contact adhesive layer during storage and prior to assembly and use.

In a further embodiment, a method for making a transdermal drug delivery system is provided, where the method involves:

providing an upper module comprising an outer backing layer, a pressure-sensitive adhesive layer laminated thereto, and a first removable release liner covering the pressure-sensitive adhesive layer;

providing a lower module comprising a porous drug reservoir layer for adhering to the pressure-sensitive adhesive layer of the upper module, and a skin-contact adhesive affixed to the drug reservoir layer;

removing the first removable release liner to expose the pressure-sensitive adhesive layer of the upper module;

loading a drug-containing formulation into the porous drug reservoir layer; and affixing the upper module to the lower module by contacting the exposed pressure-sensitive layer of the upper module to the drug-loaded porous drug reservoir layer.

In a related embodiment, the method for making a transdermal drug delivery system involves:

providing an upper module as above;

providing a lower module comprising a porous drug reservoir layer for adhering to the pressure-sensitive adhesive layer of the upper module upon assembly, a skin-contact adhesive affixed to the drug reservoir layer, and, contained within the porous drug reservoir layer, a formulation containing a pharmacologically active agent or a precursor thereto;

removing the first removable release liner to expose the pressure-sensitive adhesive layer of the upper module; and affixing the upper module to the lower module by contacting the exposed pressure-sensitive layer of the upper module to the drug-loaded porous drug reservoir layer.

In a further embodiment, the invention provides a plurality of components that can be assembled into a transdermal drug delivery system, comprising:

an upper module comprising an outer backing layer, a pressure-sensitive adhesive layer laminated thereto, and a first removable release liner covering the pressure-sensitive adhesive layer; and at least two lower modules each comprising a porous drug reservoir layer that can adhere to the pressure-sensitive adhesive layer of the upper module and into which a pharmaceutical formulation will be loaded, and a skin-contact adhesive affixed to the drug reservoir layer, wherein the lower modules differ from each other in at least one respect, such as total thickness, reservoir volume, or the presence of one or more additional layers, but wherein the upper module can be assembled with any one of the lower modules to provide a laminated transdermal delivery system.

In a related embodiment, the invention provides a plurality of components that can be assembled into a transdermal drug delivery system, comprising:

an upper module comprising an outer backing layer, a pressure-sensitive adhesive layer laminated thereto, and a first removable release liner covering the pressure-sensitive adhesive layer; and at least two lower modules each comprising a porous drug reservoir layer for adhering to the pressure-sensitive adhesive layer of the upper module upon assembly, a skin-contact adhesive affixed to the drug reservoir layer, and, contained within the porous drug reservoir layer, a formulation containing a pharmacologically active agent or precursor thereto, wherein the lower modules differ from each other in at least one respect, such as the active agent or agents in the drug reservoir layer, the total thickness of the module, the volume of the drug reservoir layer, or, as above, the presence of one or more additional layers, but wherein the upper module can be assembled with any one of the lower modules to provide a laminated transdermal delivery system.

In another embodiment, the invention provides a plurality of components that can be assembled into a transdermal drug delivery system, comprising:

at least two upper modules each comprising an outer backing layer, a pressure-sensitive adhesive layer laminated thereto, and a first removable release liner covering the pressure-sensitive adhesive layer, where the upper modules differ from each other in at least one respect; and a lower module comprising a porous drug reservoir layer that can adhere to the pressure-sensitive adhesive layer of an upper module and into which a pharmaceutical formulation will be loaded, and a skin-contact adhesive affixed to the drug reservoir layer, wherein the lower module can be assembled with any one of the upper modules to provide a laminated transdermal delivery system.

In another embodiment, the invention provides a plurality of components that can be assembled into a transdermal drug delivery system, comprising:

at least two upper modules each comprising an outer backing layer, a pressure-sensitive adhesive layer laminated thereto, and a first removable release liner covering the pressure-sensitive adhesive layer, where the upper modules differ from each other in at least one respect; and a lower module comprising a porous drug reservoir layer that can adhere to the pressure-sensitive adhesive layer of an upper module, a skin-contact adhesive affixed to the drug reservoir layer, and, contained within the porous drug reservoir layer, a formulation containing a pharmacologically active agent or a precursor thereto, wherein the lower module can be assembled with any one of the upper modules to provide a laminated transdermal delivery system.

In a further embodiment, a modular transdermal delivery system is provided that includes the following elements:

an upper module comprising an outer backing layer and a pressure-sensitive adhesive layer laminated thereto; and, affixed to the pressure-sensitive adhesive layer, a lower module comprising a porous drug reservoir that is adhered to the pressure-sensitive adhesive layer, a skin contact adhesive underlying the drug reservoir layer that serves as the basal surface of the system in contact with the skin during drug delivery, and, contained within the porous drug reservoir layer, a formulation containing a pharmacologically active agent or precursor thereto.

In another embodiment, the invention provides a method for administering a pharmacologically active agent to an individual, wherein the method involves applying to the skin of the individual a modular transdermal delivery system that includes the following elements:

an upper module comprising an outer backing layer and a pressure-sensitive adhesive layer laminated thereto; and, affixed to the pressure-sensitive adhesive layer, a lower module comprising a porous drug reservoir that is adhered to the pressure-sensitive adhesive layer, a skin contact adhesive underlying the drug reservoir layer that serves as the basal surface of the system in contact with the skin during drug delivery, and, contained within the porous drug reservoir layer, a formulation containing a pharmacologically active agent to be administered or a precursor thereto.

Additional features and objects of the invention are set forth in part in the description that follows, and in part will become apparent to those skilled in the art upon examination of the following.

DETAILED DESCRIPTION OF THE INVENTION

I. Definitions and Nomenclature

Unless defined otherwise, all technical and scientific terms used herein have the meaning commonly understood by one of ordinary skill in the art to which the invention pertains. Specific terminology of particular importance to the description of the present invention is defined below.

In this specification and the appended claims, the singular forms "a," "an" and "the" include plural referents unless the context clearly dictates otherwise. Thus, for example, reference to "a pharmacologically active agent" or simply "an active agent" includes a single such agent as well as two or more such agents; "a pharmaceutically acceptable carrier" refers to a combination of pharmaceutically acceptable carriers as well as to a single pharmaceutically acceptable carrier; "a formulation" and "a vehicle" includes two or more formulations and vehicles, respectively, and the like.

When referring to an active agent, whether specified as a particular compound or a compound class, the term used to refer to the agent is intended to encompass not only the specified molecular entity but also its pharmaceutically acceptable, pharmacologically active analogs and derivatives, including, but not limited to, salts, esters, amides, prodrugs, conjugates, active metabolites, hydrates, crystalline forms, enantiomers, stereoisomers, and other such derivatives, analogs, and related compounds.

By "transdermal" delivery, applicants intend to include both transdermal (or "percutaneous") and transmucosal administration, i.e., delivery by passage of a pharmacologically active agent through the skin or mucosal tissue and into the bloodstream, thereby providing a systemic effect. "Topical" delivery generally refers to delivery of an active agent to the skin surface and thus the uppermost region of the skin, and provides a local rather than systemic effect, as the agent does not penetrate into the bloodstream. The present modular system is applied "topically" insofar as it is affixed to a body surface, but depending on the active agent and the components of the formulation containing the active agent (such as one or more penetration enhancers), drug delivery may be either transdermal or topical and thus either systemic or local. Accordingly, unless otherwise specified herein, reference to the modular "transdermal system" encompasses a system that can be used for either transdermal delivery or topical delivery, and reference to "transdermal delivery" encompasses a method that can be adapted for either transdermal or topical drug administration.

The terms "treating" and "treatment" as used herein refer to the administration of a pharmaceutical agent or composition to a subject to provide a desired pharmacological or physiological effect, and thus encompasses administration for therapeutic and/or prophylactic purposes. Treating a condition in a subject already suffering from that condition generally involves a reduction in the severity, number, and/or frequency of symptoms, the elimination of symptoms and/or underlying cause, and the improvement or remediation of damage. In the prophylactic context, treatment refers to the administration of a pharmaceutical agent or composition to a subject who is not yet suffering from a particular condition, but has been identified as at susceptible to, i.e., at risk for developing, the particular condition, where the prophylactic effect involves partially or completely preventing a condition or symptom thereof.

The terms "effective amount" and "therapeutically effective amount" of an active agent, an active agent combination, or a pharmaceutical formulation refer to an amount that is nontoxic but sufficient for producing a desired result. The exact amount required will vary from subject to subject, depending on factors such as the age, weight and general condition of the subject, the particular condition being treated, the severity of the condition, the specific active agent, and, of course, the judgment of the clinician. In the present context, the effective amount typically ranges from about 0.05 mg to about 15,000 mg, preferably about 0.1 mg to about 1,000 mg, and usually about 0.1 mg to about 500 mg, per day.

By "pharmaceutically acceptable" is meant a material that is not biologically or otherwise undesirable, i.e., the material may be incorporated into a pharmaceutical composition as provided herein and not cause any substantial undesirable biological effects or interact in a deleterious manner with any of the other components of the composition. When the term "pharmaceutically acceptable" is used to refer to a pharmaceutical carrier or excipient, it is implied that the carrier or excipient has met the required standards of toxicological and manufacturing testing and/or that it is included on the Inactive Ingredient Guide prepared by the U.S. Food and Drug administration.

"Pharmacologically active" as in a "pharmacologically active agent" (also referred to herein as simply an "active agent") refers to a structural analog having the same type of pharmacological activity as the parent compound and approximately equivalent in degree.

As used herein, "subject" or "individual" or "patient" refers to any subject to whom an active agent is to be administered transdermally to achieve a beneficial effect. The subject can be any vertebrate, but will typically be a mammal, and for most purposes will be human.

The term "combination" to refer to a "combination" of two or more active agents may refer to a mixture or blend of the active agents, as may be present in a single pharmaceutical formulation. The term may also refer to two or more active agents that are contained in the same transdermal delivery system but in separate regions of the system, e.g., in separate layers of a laminated system. The term "combination" when used in the context of a method of use encompasses simultaneous administration of two or more active agents, which may or may not be present in a single pharmaceutical formulation, and separate, i.e., sequential administration of the two or more active agents, as would be the case when a first active agent is released into the skin from one layer of a transdermal system, and a second active agent is released into the skin at a different time, from the same layer as the first active agent or from a different layer.

II. The Modular System

Figure 1:
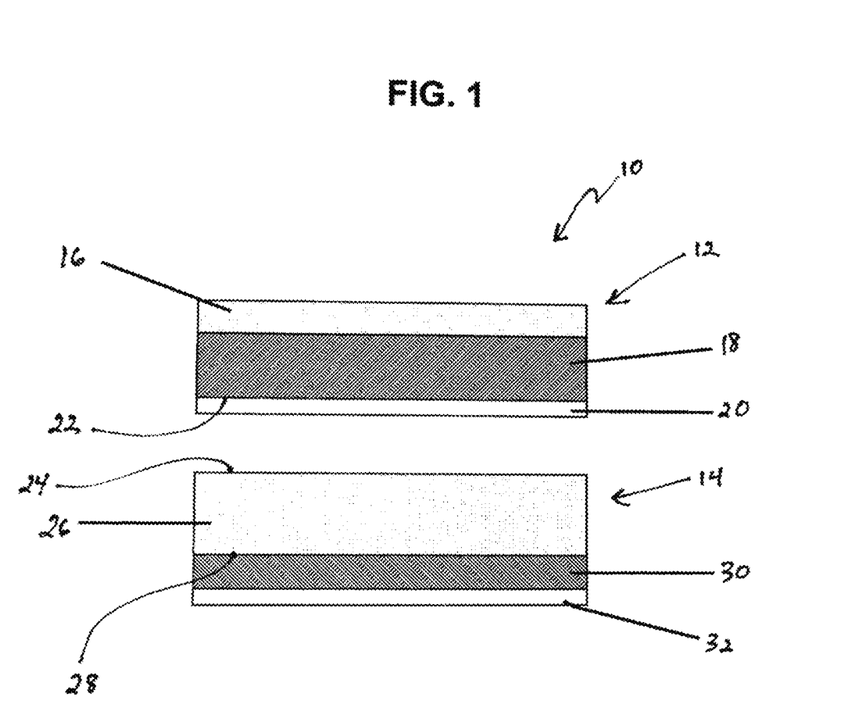
FIG. 1 schematically illustrates lower and upper modules of a pre-assembled modular transdermal drug delivery system of the invention.

One embodiment of the modular system of the invention is illustrated in FIG. 1. The system 10 is composed of an upper module 12 and a lower module 14.

The upper module 12 includes a backing layer 16, a pressure-sensitive adhesive (PSA) layer 18 laminated thereto, and a first release liner 20 covering the otherwise exposed PSA surface 22 for protection but readily removable prior to assembly and use. Note that FIG. 1 is not to scale, and the various layers may have different relative thicknesses than those shown. For example, layer 18 is normally a thin layer that just connects the two adjacent layers; that is, layer 18 does not have any substantial thickness unless it is used as a reservoir for an additional drug or other type of compound, e.g., an activator of a drug precursor, as discussed infra.

The backing layer 16 is typically, although not necessarily, the primary structural element of the transdermal system following assembly, and can be selected so as to provide the device with physical characteristics such as flexibility, drape, and, if desired, occlusivity. The material selected to serve as the backing layer should be stable under storage conditions, chemically inert with respect to any components of the PSA layer laminated thereto, and incapable of absorbing formulations and formulation components contained within the PSA or elsewhere within the assembled system. The backing is preferably made of one or more sheets or films of a flexible elastomeric material that serves as a protective covering to prevent loss of drug and/or vehicle via transmission through the upper surface of the assembled system. In addition, the backing material may be chosen to impart a degree of occlusivity to the device, such that the area of the skin covered on application becomes hydrated. The material used for the backing layer should permit the assembled transdermal system to follow the contours of the skin and be worn comfortably on areas of skin such as at joints or other points of flexure, areas that are normally subjected to mechanical strain, with little or no likelihood of the system disengaging from the skin due to differences between the flexibility or resiliency of the skin and the flexibility or resiliency of the system.

Examples of materials useful for the backing layer are polyesters, polyethylene, polypropylene, polyurethanes, polyether amides, and ethylene-vinyl acetate copolymers (EVA). Backing layers may be obtained commercially, for instance under the Scotchpak™ and CoTran™ brands from 3M Corporation, including polyester film backings (3M Scotchpak™ 9754, 9757, and 9758), polyester film laminate backings (3M Scotchpak™ 1012, 9723, 9730, 9733, 9735, and 9738), polyurethane nonwoven backings (3M CoTran™ 9700), polyurethane monolayer film backings (3M CoTran™ 9701), and polyethylene monolayer film backings (3M CoTran™ 9718, 9719, 9720, and 9722).

The backing layer is generally in the range of about 10 microns to about 300 microns in thickness, preferably in the range of about 15 microns to about 250 microns in thickness, and may, if desired, be pigmented, metallized, or provided with a matte finish suitable for writing.

PSA layer 18, laminated to the backing layer 16, provides the means for securing the upper module 12 to the lower module 14 upon assembly of the transdermal system, which requires joinder of the two modules. That is, as first release liner 20 is removed from the underside of the upper module 12, the PSA surface 22 is exposed and enables joinder with the upper surface 24 of the lower module 14. The PSA layer 18 is comprised of a pressure-sensitive adhesive composition that not only facilitates a firm adhesive bond with surface 24 of the lower module, but also is physically and chemically compatible with the pharmacologically active agent, the active agent formulation, and any other formulation or vehicle that will be loaded into the system. PSA layer 18 generally ranges in thickness from about 10 to about 100 microns, typically about 10 to about 50 microns.

The PSA composition preferably includes a visco-elastic polymer, such as may be selected from polysiloxanes (silicones), polyisobutylenes (PIBs), polyacrylates, polyurethanes, and tacky rubbers other than PIB, such as polystyrene-isoprene copolymers, polystyrene-butadiene copolymers, and mixtures thereof. In addition to the elastomeric polymer, the PSA composition can also include a tackifying resin, a filler, a stabilizer and/or antioxidant, and a cross-linking agent, all selected to provide the desired degree of tack, peel adhesion, skin adhesion, and cohesive strength. The PSA composition should exhibit low partitioning for the active agent in the assembled transdermal system, so that, during drug delivery, the pharmaceutical formulation containing the agent will permeate downward through the assembled transdermal system, toward the skin, rather than moving upward into the PSA layer. Thus, for instance, the PSA might be made more hydrophilic with an active agent that is lipophilic, e.g., a cannabinoid or saxitoxin; this may be accomplished by the introduction of a hydrophilic compound or composition into the PSA layer. Conversely, the PSA can be made more lipophilic for delivery of a water-soluble or at least somewhat hydrophilic active agent, such as by introduction of a mineral oil or other lipophilic vehicle into the PSA. Ideally, the PSA composition should be selected so that greater than 90 wt. % of the active agent formulation in the reservoir passes downward toward the skin, preferably greater than 95 wt. %., with minimal (less than 10 wt. %, preferably less than 5 wt. %) movement upward into the PSA.

PSA layer 18 may also include one or more of the following: a skin permeation enhancer; a composition that otherwise modifies the permeation rate of the active agent through one or more layers of the assembled system; a composition that modifies the release rate of the active agent; and/or a compound that acts as an activator (as described elsewhere herein) to convert a precursor of an active agent to the active form.

Subsequent to assembly and drug delivery, and thus after the transdermal system has been substantially depleted of drug, the upper and lower modules can be separated and reused, by recombination with each other or with other upper or lower modules. In this case, the PSA composition should be selected such that while it facilitates adhesion of the upper module to the lower module prior to and during use, using no more than applied finger pressure, it also has sufficient cohesive strength that it allows separation of the modules without rupture and without leaving a residue on either surface.

First release liner 20 is a disposable element that serves to protect the underside of the upper module 12 prior to joinder with the lower module 14, and covers the otherwise exposed PSA surface 22. Typically, the release liner is formed from a chemically inert material that is occlusive or at least impermeable to the pharmacologically active agents, formulations, and vehicles that will be loaded into the system prior to assembly and use. Release liners are typically composed of polyesters or other polymers that are treated with silicone coatings, fluorosilicone coatings, or coatings of other fluoropolymers. Commercially available release liners are available, and include, by way of example, Syl-Off® products (available from the Dow Corning Corporation), Tribex Corporation products, and 3M Scotchpak™ products.

The release liner 20 is preferably scored or perforated, to allow the release liner to be removed in two parts. This facilitates proper alignment of the lower module to the upper module prior to adhesion, minimizing accidental adhesion in a mis-aligned configuration. The scoring line or perforation can be centered or off-center; if off-center, the smaller segment of the release liner can be removed first, thus exposing less than half of the pressure-sensitive adhesive layer, while the modules are aligned and then partially adhered, with the exposed PSA layer adhering to the corresponding surface of the upper module. The release liner segment can be removed and attachment completed. Optionally, at least one score mark (e.g., a small circle, two squares, or the like) may be incorporated into the upper surface of the lower module to facilitate alignment of the upper and lower modules.

The lower module 14 is composed of a porous drug reservoir layer 26 that has an upper surface 24 and an opposing lower surface 28 laminated to a skin contact adhesive (SCA) layer 30, which is in turn protected, prior to use, with a second removable release liner 32.

The uppermost layer of lower module 14 thus serves as a drug reservoir and is composed of a porous material, where the material has an average pore size in the range of about 1 nm to about 50 nm, typically in the range of about 1 nm to about 20 nm, preferably in the range of about 1 nm to about 5 nm, optimally in the range of about 1 nm to about 2.5 nm. Porous materials with average pore size in the range of about 1 nm to about 2.5 nm, are typically referred to as "microporous" materials, and, as noted, are preferred herein. The preferred pore volume (i.e., void percentage) is usually in the range of about 10% to about 60%.

In one embodiment, the drug reservoir 26 is fabricated so that it has a defined porosity or void volume, i.e., the reservoir layer can hold a predetermined weight of active agent per unit area, which may be, for example, in the range of about 10 µg/cm² to about 100 µg/cm². In other cases, depending on the active agent, other formulation components, and the desired pharmacokinetic profile, the predetermined weight of active agent per unit area may be outside of the aforementioned range.

The reservoir can be selected to have a specific void volume or capacity to hold the desired load volume needed for the therapeutic application. The reservoir may also have a porosity gradient, wherein the uppermost region of the reservoir layer is more porous, with porosity gradually decreasing through the body of the layer so that the lowermost region of the reservoir layer is the least porous region. This is useful in controlling the flux of one or more formulation components out of the drug reservoir. The porosity gradient in the first case is isotropic (i.e., symmetric), and in the second case is anisotropic (i.e., asymmetric). A third example of a porous reservoir is a composite membrane, where the selective membrane layer is chosen to create the desired release flux, while the porous support is selected to have the desired load capacity. The porosity gradient can be created using manufacturing methods known in the art, for example by adjusting the amount of porogen or other pore-creating material as the thickness of the layer is increased.

The material used for the drug reservoir may be organic and polymeric, such as microporous polypropylene (e.g., Celgard®, available from Hoechst-Celanese), microporous ethylene-vinyl acetate copolymer (e.g., CoTran®, available from 3M), microporous rayon (e.g., 3M™ 1785, 1530, and 1533 microporous rayon nonwoven fabric products), and microporous polytetrafluoroethylene (e.g., POREX®). The microporous material can also be inorganic. Suitable inorganic materials include metal oxides such as silica and titania, which are readily available from many commercial sources. The materials used can be naturally occurring, semi-synthetic, or synthetic.

The thickness of the drug reservoir layer 26 depends on the intended active agent formulation load per unit area. For example, a microporous reservoir layer 200 µm in thickness with a porosity (void volume) of 50% can hold 100 µl/cm². Typically, the thickness of the drug reservoir ranges from about 50 µm to about 2000 µm with porosities from about 20% to about 80%.

Laminated to and underlying the porous drug reservoir layer 26 is SCA layer 30. Suitable materials for the SCA may be selected from a similar class of materials appropriate for the PSA layer 18 in the upper module. As the SCA layer is designed to have a specific permeability to the active agent, i.e., a permeability within a predetermined range of permeability values, partitioning and diffusion in the SCA layer 18 may be substantially different than in PSA layer 18. The SCA composition includes a visco-elastic polymer, such as may be selected from polysiloxanes, polyisobutylenes, polyacrylates, and other polymers as described earlier in this section for layer 18; however, additional plasticizer-like compounds are typically added to modify the release flux, i.e., compounds that act to plasticize the SCA material and/or the uppermost region of the skin. Such materials include, by way of example, mineral oil; other types of oils (see, e.g., U.S. Pat. No. 5,229,1320 to Sharma et al.); fatty acids and fatty acid esters such as oleic acid and isopropyl myristate; and other lipid-based or lipid-like materials, as will be understood by those working in the field of transdermal drug delivery and transdermal formulations. It will be appreciated that certain adhesives may be preferred when the active agent is lipophilic and in an at least partially lipophilic vehicle, e.g., rubber-based adhesives, polyisobutylenes, mixtures of high molecular weight and low molecular polyisobutylenes, and the like. See, e.g., U.S. Pat. No. 5,508,038 to Wang et al., the disclosure of which is incorporated by reference herein. Analogously, other adhesives may be preferred when the active agent is hydrophilic and in an at least partially hydrophilic vehicle, e.g., polyacrylates and polyurethanes. In addition to the elastomeric polymer, the SCA composition can also include a tackifying resin, a filler, a stabilizer and/or antioxidant, and a cross-linking agent, as above. As the SCA layer contacts the skin and provides the means for affixing the transdermal system to the skin during drug delivery, materials that are likely to cause skin irritation and/or sensitization should obviously be avoided. When any formulation components are required that may result in such a skin reaction, an anti-irritant, emollient, or the like, may be incorporated into the SCA to offset, minimize, or prevent the adverse effect.

SCA layer 30 can also serve as a second drug reservoir, insofar as it may be loaded or pre-loaded with a pharmaceutical formulation for delivery to the skin, where the pharmaceutical formulation contains a pharmacologically active agent. The active agent may be the same as the active agent in porous drug reservoir layer 26, in which case it may be present in the same formulation or in a different formulation, at the same concentration or a different concentration. Alternatively, the active agent may be different from the active agent in the porous drug reservoir, in which case the two active agents are co-administered, either simultaneously, or, depending on the structure of the system, the thickness of the layers, and the components of the active agent formulations (e.g., enhancers, activators, rate-controlling membranes and species, or the like), sequentially. In an alternative embodiment, the SCA can be a peripheral ring placed adjacent to the outer edges of the lower module, rather than being a layer that extends across the entirety of the lower surface of the module.

Like PSA layer 18, the SCA layer 30 may also include a skin permeation enhancer; a composition that otherwise modifies the permeation rate of the active agent through the SCA and/or through any additional layer incorporated into the system below the drug reservoir layer 26; a composition that modifies the release rate of the active agent; and/or a compound that acts as an activator (as described elsewhere herein) to convert a precursor of an active agent to the active form.

Prior to use, a second removable release liner 32 covers and thereby protects the SCA. The second release liner may or may not be identical to first release liner 20. Upon removal of second release liner 32, serves as the basal surface of the transdermal system, which, as explained above, adheres to the skin. The second release liner may be perforated or scored to facilitate removal, as described earlier with respect to the first release liner 20.

The transdermal system may contain additional layers, including additional drug reservoirs, which may or may not be of the matrix type; additional matrix layers and/or adhesive layers; fabric layers, and rate-controlling membranes. Any of these layers may be incorporated into the upper module, the lower module, or both.

A rate-controlling membrane, as is known in the art, is selected so that a component of the transdermal system, generally the pharmacologically active agent, diffuses through the membrane at a finite, controllable rate. The rate-controlling membrane can be porous or nonporous, or may contain fluid-filled micropores. By varying the composition and/or thickness of the membrane, the rate of release of active agent (or other component) from the membrane can be controlled. Representative materials useful for forming rate-controlling membranes include polyolefins such as polyethylene and polypropylene, polyamides, polyesters, ethylene-ethacrylate copolymer, ethylene-vinyl acetate copolymer, ethylene-vinyl methylacetate copolymer, ethylene-vinyl ethylacetate copolymer, ethylene-vinyl propylacetate copolymer, polyisoprene, polyacrylonitrile, ethylene-propylene copolymer, silicone rubber, polyester polyurethanes, polyether urethanes, and the like.

The dimensions of the transdermal system are generally such that the basal surface of the system has an area in the range of about 5 $cm^2$ to about 100 $cm^2$, preferably in the range of about 10 $cm^2$ to about 80 $cm^2$, e.g., about 15 $cm^2$ to about 25 $cm^2$. Other dimensions can vary as well, and both the lower and upper modules may be constructed so as to contain additional layers and/or layers of varying thickness. For instance, lower modules can be made with different reservoir thicknesses, which in turn allows additional formulation and/or pharmacologically active agent to be loaded into the system. This modularity—where lower and upper modules can essentially be provided as components of a "mix and match" system"—is advantageous insofar as a downstream assembler or user of the system can affix any one of a plurality of lower modules to a given upper module depending on the loading volume or delivery characteristics desired in an individual case. This feature of the invention provides tremendous flexibility and can be used for example in the process of dose escalation or titration.

The modular segments can be manufactured in any desired size or shape, e.g., by manufacture in the form of a sheet that can be cut into any of a variety of shapes and sizes. Examples of shapes include simple shapes such as squares, rectangles, circles and ovals, as well as more complicated shapes adapted for a particular purpose, e.g., for delivery of a wound-healing agent to a wound having a particular shape (such as a crescent or L-shape), or for delivery to a particular part of the body, e.g., a facial mask with suitable apertures for eyes, nose, and mouth, such as in the delivery of one or more cosmeceutical agents to the face.

Specifically, should a physician or other medical practitioner decide at some point during the drug delivery period, or even prior to drug delivery, that a patient requires a modification in dosage regimen, an upper module can be combined with a lower module that contains a higher or lower dosage of the active agent, as necessary. Additionally, should it be desirable or necessary to administer two active agents in combination, either simultaneously or sequentially, from the same transdermal system, an upper module with a first active agent loaded into the PSA layer or other layer that serves as an upper drug reservoir, can be combined with a lower module containing the second active agent loaded into porous drug reservoir. The modularity of the transdermal system also facilitates re-use of either or both of the modular components, as well as refilling of the modules once the initial quantity of active agent is depleted.

III. Formulations and Formulation Components

The modular transdermal delivery system of the invention contains a pharmaceutical formulation loaded into the porous drug reservoir prior to assembly. Other types of formulations can be loaded into other layers of the modules, as will be explained infra.

The pharmaceutical formulation comprises an effective amount of a pharmacologically active agent, wherein that amount is equivalent to an amount somewhat higher than the total dose to be administered over the drug delivery period. That is, to assure a stable, approximately constant driving force and to avoid early depletion of active agent, an "overage" of the active agent is typically loaded into the drug reservoir, typically on the order of three times the intended total dose, or higher. For instance, for delivery at 10 $\mu g/cm^2$, a load of at least 30 $\mu g/cm^2$ should be in the drug reservoir, unless a reduction of delivery flux during the drug delivery period is desired, e.g., to avoid tolerance. The total intended dose, i.e., the total active agent released into the skin over the entirety of the drug delivery period, is predetermined and dependent on the particular drug, patient, condition, severity of the condition, and the like. Other factors, specific to transdermal drug delivery, include the solubility and permeability of the active agent or active agents in the formulations and layers of the drug delivery system, and the period of time for which the system will be affixed to the skin. The minimum effective amount of the pharmacologically active agent is determined by the requirement that sufficient quantities of the agent must be present to maintain the desired rate of release over the given period of drug delivery. The maximum amount for safety purposes is determined by the requirement that the quantity of active agent present cannot exceed a rate of release that reaches toxic levels. Generally, the maximum concentration is determined by the amount of agent that can be loaded into the drug reservoir without producing adverse histological effects such as irritation or sensitization, an unacceptably high initial pulse of agent released into the body, or adverse effects on the characteristics of the transdermal system such as the loss of tackiness, alteration of viscosity, or deterioration of other properties.

The pharmacologically active agent may be any compound that is suitable for topical, transdermal or transmucosal delivery and induces a desired local or systemic effect. Such agents include the broad classes of compounds normally delivered through body surfaces and membranes, including skin. In general, this includes: analgesic agents; anesthetic agents; antiarthritic agents; respiratory drugs, including antiasthmatic agents; anticancer agents, including antineoplastic drugs; anticholinergics; anticonvulsants; antidepressants; antidiabetic agents; antidiarrheals; antihelminthics; antihistamines; antihyperlipidemic agents; antihypertensive agents; anti-infective agents such as antibiotics and antiviral agents; anti-inflammatory agents; antimigraine preparations; antinauseants; antineoplastic agents; antiparkinsonism drugs; antipruritics; antipsychotics; antipyretics; antispasmodics; antitubercular agents; antiulcer agents; antiviral agents; anxiolytics; appetite suppressants; attention deficit disorder (ADD) and attention deficit hyperactivity disorder (ADHD) drugs; cardiovascular preparations including calcium channel blockers, CNS agents; beta-blockers and antiarrhythmic agents; central nervous system stimulants; cough and cold preparations, including decongestants; diuretics; genetic materials; herbal remedies; hormonolytics; hypnotics; hypoglycemic agents; immunosuppressive agents; leukotriene inhibitors; mitotic inhibitors; muscle relaxants; narcotic antagonists; nicotine; nutritional agents, such as vitamins, essential amino acids and fatty acids; ophthalmic drugs such as antiglaucoma agents; parasympatholytics; peptide drugs; psychostimulants; sedatives; steroids; sympathomimetics; tranquilizers; vasodilators including general coronary, peripheral and cerebral, and wound-healing agents. The active agent administered also may be one that is cosmetically or "cosmeceutically" effective, as will be explained infra with regard to topically active agents. Such agents include, for example, compounds that can reduce the appearance of aging or photodamaged skin, e.g., antioxidants, moisturizers, collagen or hyaluronic acid, and alpha hydroxyacids. Other active agents that exert a cosmeceutically beneficial effect are PSP toxins, e.g., carbamoyl saxitoxins, sulfamate saxitoxins, and decarbamoyl saxitoxins, with the carbamoyl saxitoxin group preferred; the latter group includes, by way of example, the gonyautoxins (also referred to as gonytoxins). See Hall et al., "The Saxitoxins," in *Marine Toxins, Origin, Structure, and Molecular Pharmacology*, Eds. Hall et al., Ch. 3 (ACS Symposium Series 418, American Chemical Society, Washington D.C. 1990).

The active agent may be administered, if desired, in the form of a salt, ester, amide, prodrug, conjugate, active metabolite, hydrate, crystalline form, enantiomer, stereoisomer, or the like, provided that the salt, ester, amide, etc. is suitable pharmacologically and/or can be converted into a pharmacologically suitable form within the transdermal system itself. For example, this may be accomplished by incorporating an activator compound or composition in the upper module, generally in the PSA layer, where that activator is selected to convert a drug precursor in the drug reservoir to a pharmacologically active form prior to release from the system and delivery into the body surface. For instance, the drug precursor in the reservoir may be an inactive esterified form of an active agent that exists in active form as a carboxylic acid, and the activator may be a compound or composition such as a weak base that brings about de-esterification to generate the drug in active form, i.e., as the activator passes down through the system and thus through the drug reservoir containing the drug precursor. As another example, the drug precursor in the reservoir may be an inactive imine form of a pharmacologically active primary amine, and the activator may be a slightly acidic aqueous solution that converts the imine to the active primary amine prior to drug release from the system into the skin. Other examples will be apparent to those of ordinary skill in the art and/or are described in the pertinent texts and literature, e.g., Greene's Protective Groups in Organic Synthesis, 5th edition, Wuts, J., Ed. (Wiley, 2014); H. Bundgaard, Design of Prodrugs (Elsevier, 1985); and J. March, Advanced Organic Chemistry: Reactions, Mechanisms and Structure, 4th Ed. (New York: Wiley-Interscience, 1992).

Specific pharmacologically active agents of interest that may be administered using the transdermal systems of the invention include, by way of example and not limitation, those set forth below.

Anti-microbial agents: Tetracycline antibiotics and related compounds (e.g. chlortetracycline, oxy-tetracycline, demeclocycline, methacycline, doxycycline, minocycline and roli-tetracycline); macrolide antibiotics such as erythromycin, clarithromycin, and azithromycin; streptogramin antibiotics such as quinupristin and dalfopristin; beta-lactam antibiotics, including penicillins (e.g., penicillin G, penicillin VK), antistaphylococcal penicillins (e.g. cloxacillin, dicloxacillin, nafcillin and oxacillin), extended spectrum penicillins (e g aminopenicillins such as ampicillin and amoxicillin, and antipseudomonal penicillins such as carbenicillin), cephalosporins (e.g. cefadroxil, cefepime, cephalexin, cefazolin, cefoxitin, cefotetan, cefuroxime, cefotaxime, ceftazidime and ceftriaxone) and carbapenems such as imipenem, meropenem and aztreonam; aminoglycoside antibiotics such as streptomycin, gentamicin, tobramycin, amikacin and neomycin; glycopeptide antibiotics such as teicoplanin; sulfonamide antibiotics such as sulfacetamide, sulfabenzamide, sulfadiazine, sulfadoxine, sulfamerazine, sulfamethazine, sulfamethizole and sulfamethoxazole; quinolone antibiotics such as ciprofloxacin, nalidixic acid and ofloxacin; anti-mycobacterials such as isoniazid, rifampin, rifabutin, ethambutol, pyrazinamide, ethionamide, aminosalicylic and cycloserine; systemic antifungal agents such as itraconazole, ketoconazole, fluconazole and amphotericin B; and miscellaneous antimicrobial agents such as chloramphenicol, spectinomycin, polymyxin B (colistin), bacitracin, nitrofurantoin, and methenamine.

Anti-diabetic agents: Acetohexamide, chlorpropamide, ciglitazone, gliclazide, glipizide, glucagon, glyburide, miglitol, pioglitazone, tolazamide, tolbutamide, triampterine, and troglitazone.

Opioid analgesic agents: Alfentanil, buprenorphine, butorphanol, codeine, dihydrocodeine, fentanyl, hydrocodone, hydromorphone, levorphanol, meperidine, methadone, morphine, nalbuphine, oxycodone, oxymorphone, pentazocine, propoxyphene, sufentanil and tramadol.

Non-opioid analgesic agents: Apazone, etodolac, difenpiramide, indomethacin, meclofenamate, mefenamic acid, oxaprozin, phenylbutazone, piroxicam and tolmetin.

Cannabinoids: Another class of analgesic agents includes the cannabinoids, where a "cannabinoid" refers to a chemical compound that is found in the *Cannabis* genus of the Cannabaceae plant family, which includes the species *Cannabis sativa, Cannabis indica*, and *Cannabis ruderalis*, or to a metabolite, derivative, or analogue thereof, whether naturally occurring or chemically synthesized. Examples of cannabinoids that can be delivered using the present transdermal systems include tetrahydrocannabinol (THC), dronabinol (i.e., the pure isomer (−)-trans-$\Delta^9$-THC), cannabichromanone, cannabichromene (CBC), cannabichromenic acid, cannabichromevarin (CBCV), cannabichromevarinic acid, cannabicitran (CBT), cannabicoumaronone (CBCON), cannabicyclol (CBL), cannabicyclolic acid, cannabicyclovarin, cannabidiol (CBD), cannabidiol monomethyl ether, dimethyl heptylpentyl cannabidiol (DMHP-CBD), cannabidiolic acid, cannabidiorcol, cannabidivarin (CBV), cannabidivarinic acid, cannabielsoin (CBE), cannabielsoinic acid, cannabifuran, cannabigerol (CBG), cannabigerol monomethyl ether (CBGM), cannabigerolic acid, cannabigerolic acid monomethyl ether, cannabigerovarin (CBGV), cannabigerovarinic acid, cannabiglendol, cannabinodiol, cannabinodivarin, cannabinol (CBN), cannabinolic acid, cannabinol methyl ether, cannabiorcol, cannabiripsol, cannabitetrol, cannabitriol, 10-O-ethyl-cannabitriol, cannabivarichromene, cannabivarin, dehydrocannabifuran, 1,2-dihydroxyhexahydrocannabinol, 1,2-dihydroxyhexahydrocannabinol acetate, dimethylheptylpyran, isotetrahydrocannabivarin, levonantradol, nabilone, rimonabant, $\Delta^9$-tetrahydrocannabinolic acid, $\Delta^9$-tetrahydrocannabiorcol, $\Delta^9$-tetrahydrocannabiorcolic acid, $\Delta^9$-tetrahydrocannabivarin, tetrahydrocannabivarinic acid, 8,11-dihydroxy-$\Delta^9$-tetrahydrocannabinol, 8,9-dihydroxy-$\Delta^{6a,10a}$-tetrahydrocannabinol, $\Delta^8$-tetrahydrocannabinol, $\Delta^8$-isotetrahydrocannabinol, $\Delta^8$-tetrahydrocannabinolic acid, 10-oxo-$\Delta^{6a,10a}$-tetrahydrocannabinol (OTHC), HU-210 (1,1-dimethylheptyl-11-hydroxy-$\Delta^8$-THC), HU-331 (3-hydroxy-2-[(1R)-6-isopropenyl-3-methyl-cyclohex-2-en-1-yl]-5-pentyl-1,4-benzoquinone), JWH-018 (1-pentyl-3-(1-naphthoyl)indole) and other JWH cannabinoids such as JWH-073 (John W. Huffman, Clemson University, Clemson, S.C.), AM-2201 (1-(5-fluoropentyl)-3-(1-napthoyl)indole) and other AM cannabinoids (Alexandros Makriyannis Northeastern University, Boston Mass.), and CP-55,940 (2-((1S,2S,5S)-5-hydroxy-2-(3-hydroxypropyl)cyclohexyl)-5-(2-methyloctan-2-yl)phenol; Pfizer). As analgesic agents, these compounds have been proposed for use in treating neuropathic or chronic pain associated with fibromyalgia, rheumatoid arthritis, acute inflammation, and cancer. See, e.g., A. Hazekamp (2010), "Review on Clinical Studies with *Cannabis* and Cannabinoids," *Cannabinoids* 5 (special issue): 1-21. Other cannabinoids that can be delivered using the present modular transdermal system will be apparent to those of ordinary skill in the art with reference to the pertinent texts, journals, and patent literature. See, e.g., U.S. Patent Publication No. 2014/0271940 A1 to Wurzer et al., incorporated by reference herein.

Cannabinoids may be advantageously combined with one or more terpenoids, preferably although not necessarily, the naturally occurring terpenes associated with *cannabis* resin, as articulated in Wurzer et al., supra. Terpenoids include, without limitation, alloaromadendrene, allyl hexanoate, benzaldehyde, (Z)-α-cis-bergamotene, (Z)-α-trans-bergamotene, ß-bisabolol, epi-α-bisabolol, ß-bisabolene, borneol (camphol), cis-γ-bisabolene, borneol acetate (bornyl acetate), α-cadinene, camphene, camphor, cis-carveol, caryophyllene (ß-caryophyllene), α-humulene (α-caryophyllene), γ-cadinene, δ-3-carene, caryophyllene oxide, 1,8-cineole, citral A, citral B, cinnameldehyde, α-copaene (aglaiene), γ-curcumene, ß-cymene, ß-elemene, γ-elemene, ethyl decadienoate, ethyl maltol, ethyl propionate, ethylvanillin, eucalyptol, α-eudesmol, ß-eudesmol, γ-eudesmol, eugenol, cis-ß-farnesene (O-ß-farnesene), trans-α-farnesene, trans-ß-farnesene, trans-γ-bisabolene, fenchone, fenchol (norbornanol, ß-fenchol), geraniol, α-guaiene, guaiol, methyl anthranilate, methyl salicylate, 2-methyl-4-heptanone, 3-methyl-4-heptanone, hexyl acetate, ipsdienol, isoamyl acetate, limonene, linolool (linalyl alcohol, ß-linolool), α-longipinene, menthol, γ-murolene, myrcene (ß-myrcene), nerolidol, trans-nerolidol, nerol, ß-ocimene (cis-ocimene), octyl acetate, α-phellandrene, phytol, α-pinene (2-pinene), ß-pinene, pulegone, sabinene, cis-sabinene hydrate (cis-thujanol), ß-selinene, α-selinene, γ-terpinene, terpinolene (isoterpine), terpineol, terpineol-4-ol, α-terpinene (terpilene), α-thujene (origanene), vanillin, viridiflorene (ledene), and α-ylange. Analogs of these terpenoids, other naturally occurring terpenes, and semi-synthetic or wholly synthetic terpenoids, any of which may be presently known or hereinafter discovered, are also suitable for delivery using the present transdermal systems, preferably in combination with one or more cannabinoids, although delivery of one or more terpenes independent of cannabinoids is also within the scope of the invention.

Nonsteroidal anti-inflammatory agents NSAIDs): Propionic acid derivatives ketoprofen, flurbiprofen, ibuprofen, naproxen, fenoprofen, benoxaprofen, indoprofen, pirprofen, carprofen, oxaprozin, pranoprofen, suprofen, alminoprofen, butibufen, fenbufen, apazone, diclofenac, difenpiramide, diflunisal, etodolac, indomethacin, ketorolac, meclofenamate, nabumetone, phenylbutazone, piroxicam, sulindac and tolmetin; and steroidal anti-inflammatory agents, e.g., hydrocortisone, hydrocortisone-21-monoesters (e.g. hydrocortisone-21-acetate, hydrocortisone-21-butyrate, hydrocortisone-21-propionate, hydrocortisone-21-valerate), hydrocortisone-17,21-diesters (e.g. hydrocortisone-17,21-diacetate, hydrocortisone-17-acetate-21-butyrate, hydrocortisone-17,21-dibutyrate), alclometasone, dexamethasone, flumethasone, prednisolone and methylprednisolone.

Anti-convulsant agents: Azetazolamide, carbamazepine, clonazepam, clorazepate, ethosuximide, ethotoin, felbamate, lamotrigine, mephenyloin, mephobarbital, phenyloin, phenobarbital, primidone, trimethadione, vigabatrin, topiramate, and benzodiazepines.

CNS and respiratory stimulants: Xanthines such as caffeine and theophylline; amphetamines such as amphetamine, benzphetamine, dextroamphetamine, levamphetamine, and methamphetamine; and miscellaneous stimulants such as methylphenidate, modafinil, pemoline, and sibutramine.

Neuroleptic agents, including antidepressant drugs, antimanic drugs, and antipsychotic agents. Antidepressants: the tricyclic antidepressants amoxapine, amitriptyline, clomipramine, desipramine, doxepin, imipramine, maprotiline, nortriptyline, protriptyline and trimipramine; the serotonin re-uptake inhibitors (SRIs) citalopram, fluoxetine, fluvoxamine, paroxetine, sertraline and venlafaxine; monoamine oxidase (MAO) inhibitors phenelzine, tranylcypromine and (−)-selegiline; and other atypical antidepressants nefazodone, trazodone and venlafaxine. Anti-manic and anti-psychotic agents include: the phenothiazines acetophenazine, chlorpromazine, fluphenazine, mesoridazine, mesoridazine besylate, perphenazine, thioridazine, and trifluoperazine; the thioxanthenes chlorprothixene and thiothixene; and other heterocyclic drugs such as carbamazepine, clozapine, haloperidol, molindone, olanzapine, pimozide, quetiapine, risperidone and sertindole.

Anxiolytics and tranquilizers: Benzodiazepines (e.g. alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, temazepam and triazolam), buspirone, chlordiazepoxide and droperidol.

Anticancer and antineoplastic agents: Paclitaxel; docetaxel; camptothecin and its analogues and derivatives (e.g. 9-aminocamptothecin, 9-nitrocamptothecin, 10-hydroxycamptothecin, irinotecan, topotecan and 20-O-ß-glucopyranosyl camptothecin); taxanes (e.g. baccatins, cephalomannine and their derivatives); carboplatin; cisplatin; interferon α-2a, interferon α-2b, interferon α-n3 and other agents of the interferon family; levamisole; altretamine; cladribine; tretinoin; procarbazine; dacarbazine; gemcitabine; mitotane; asparaginase; porfimer; amifostine; mitotic inhibitors including podophyllotoxin derivatives teniposide and etoposide; and the vinca-alkaloids vinorelbine, vincristine and vinblastine.

Antihyperlipidemic agents: HMG-CoA reductase inhibitors such as atorvastatin, simvastatin, pravastatin, lovastatin and cerivastatin, and other lipid-lowering agents clofibrate, fenofibrate, gemfibrozil and tacrine.

Anti-hypertensive agents: Amlodipine, benazepril, darodipine, dilitazem, diazoxide, doxazosin, enalapril, eposartan, losartan, valsartan, felodipine, fenoldopam, fosinopril, guanabenz, guanethidine, guanfacine, hydralazine, metyrosine, minoxidil, nicardipine, nifedipine, nisoldipine, phenoxybenzamine, prazosin, quinapril, reserpine and terazosin.

Cardiovascular preparations: Angiotensin converting enzyme (ACE) inhibitors such as enalapril, 1-carboxymethyl-3-1-carboxy-3-phenyl-(1S)-propylamino-2,3,4,5-tetrahydro-1H-(3S)-1-benzazepine-2-one, 3-(5-amino-1-carboxy-1-S-pentyl)amino-2,3,4,5-tetrahydro-2-oxo-3-S-1-H-benzazepine-1-acetic acid or 3-(1-ethoxycarbonyl-3-phenyl-(1S)-propylamino)-2,3,4,5-tetrahydro-2-oxo-(-3S)-benzazepine-1-acetic acid monohydrochloride; the cardiac glycosides digoxin and digitoxin; inotropes such as amrinone and milrinone; the calcium channel blockers verapamil, nifedipine, nicardipene, felodipine, isradipine, nimodipine, bepridil, amlodipine and diltiazem; the beta-blockers atenolol, metoprolol; pindolol, propafenone, propranolol, esmolol, sotalol, timolol and acebutolol; antiarrhythmics including moricizine, ibutilide, procainamide, quinidine, disopyramide, lidocaine, phenyloin, tocainide, mexiletine, flecainide, encainide, bretylium and amiodarone; cardioprotective agents such as dexrazoxane and leucovorin; vasodilators such as nitroglycerin; and the diuretic agents hydrochlorothiazide, furosemide, bumetamide, ethacrynic acid, torsemide, azosemide, muzolimine, piretanide and tripamide.

Anti-viral agents: These include anti-herpes agents such as acyclovir, famciclovir, foscarnet, ganciclovir, idoxuridine, sorivudine, trifluridine, valacyclovir and vidarabine; anti-retroviral agents such as didanosine, stavudine, zalcitabine, tenovovir and zidovudine; and other antiviral agents including amantadine, interferon-α, ribavirin and rimantadine.

Sex steroids: The progestogens acetoxypregnenolone, allylestrenol, anagestone acetate, chlormadinone acetate, cyproterone, cyproterone acetate, desogestrel, dihydrogesterone, dimethisterone, ethisterone (17α-ethinyl-testosterone), ethynodiol diacetate, fluorogestone acetate, gestadene, hydroxyprogesterone, hydroxyprogesterone acetate, hydroxyprogesterone caproate, hydroxymethylprogesterone, hydroxymethylprogesterone acetate, 3-ketodesogestrel, levonorgestrel, lynestrenol, medrogestone, medroxyprogesterone acetate, megestrol, megestrol acetate, melengestrol acetate, norethindrone, norethindrone acetate, norethisterone, norethisterone acetate, norethynodrel, norgestimate, norgestrel, norgestrienone, normethisterone and progesterone. Also included within this class are estrogens, e.g. β-estradiol (i.e. 1,3,5-estratriene-3,17β-diol, or 17β-estradiol) and its esters, including estradiol benzoate, valerate, cypionate, heptanoate, decanoate, acetate and diacetate; 17α-estradiol; ethinylestradiol (i.e. 17α-ethinylestradiol) and esters and ethers thereof, including ethinylestradiol-3-acetate and ethinylestradiol-3-benzoate; estriol and estriol succinate; polyestrol phosphate; estrone and its esters and derivatives, including estrone acetate, estrone sulfate, and piperazine estrone sulfate; quinestrol; mestranol; and conjugated equine estrogens. Androgenic agents, also included within the class of sex steroids, are drugs such as the naturally-occurring androgens androsterone, androsterone acetate, androsterone propionate, androsterone benzoate, androstenediol, androstenediol-3-acetate, androstenediol-17-acetate, androstenediol-3,17-diacetate, androstenediol-17-benzoate, androstenediol-3-acetate-17-benzoate, androstenedione, dehydroepiandrosterone (DHEA or prasterone), sodium dehydro-epiandrosterone sulfate, 4-dihydrotestosterone (DHT or stanolone), 5α-dihydrotestosterone, dromostanolone, dromostanolone propionate, ethylestrenol, nandrolone phenpropionate, nandrolone decanoate, nandrolone furylpropionate, nandrolone cyclohexanepropionate, nandrolone benzoate, nandrolone cyclohexanecarboxylate, oxandrolone, stanozolol and testosterone; pharmaceutically acceptable esters of testosterone and 4-dihydrotestosterone, typically esters formed from the hydroxyl group present at the C-17 position, including, but not limited to, the enanthate, propionate, cypionate, phenylacetate, acetate, isobutyrate, buciclate, heptanoate, decanoate, undecanoate, caprate and isocaprate esters; and pharmaceutically acceptable derivatives of testosterone methyl testosterone, testolactone, oxymetholone and fluoxymesterone.

Muscarinic receptor modulators: Choline esters such as acetylcholine, methacholine, carbachol, bethanechol (carbamylmethylcholine), bethanechol chloride, cholinomimetic natural alkaloids and synthetic analogues thereof, including pilocarpine, muscarine, and oxotremorine; muscarinic receptor antagonists including *belladonna* alkaloids or semi-synthetic or synthetic analogues thereof, atropine, scopolamine, homatropine, homatropine methyl bromide, ipratropium, methantheline, methscopolamine and tiotropium.

Agents to treat neurodegenerative diseases: Active agents for treating Alzheimer's disease and Huntington's disease include donezepil, physostigmine, and tacrine, for treatment of Alzheimer's Disease, and fluoxetine and carbamazepine, for treating Huntington's Disease. Anti-Parkinsonism drugs useful herein include amantadine, apomorphine, bromocriptine, levodopa (particularly a levodopa/carbidopa combination), pergolide, ropinirole, selegiline, trihexyphenidyl, trihexyphenidyl hydrochloride, and anticholinergic agents. ALS is generally treated with spasmolytic (anti-spastic) agents such as baclofen, diazepam, tizanidine, and dantrolene.

Appetite suppressants: These include amphetamine, dextroamphetamine, dextroamphetamine sulfate, diethylpropion, mazindol, methamphetamine, and phentermine.

Genetic material and other biomolecules may also be delivered using the transdermal systems of the invention. Genetic material includes, for example, a nucleic acid, RNA, DNA, recombinant RNA, recombinant DNA, antisense RNA, antisense DNA, a ribooligonucleotide, a deooxyriboonucleotide, an antisense ribooligonucleotide, an antisense deoxyribo-oligonucleotide, or the like. Other biomolecules of interest for delivery using the present transdermal systems include peptidyl drugs, i.e., compounds having a molecular structure comprised of at least one amino acid. Although any peptidyl active agent may be incorporated into the delivery systems of the present invention, the drug is generally selected from coagulation modulators, cytokines, endorphins, kinins, hormones, LHRH (luteinizing hormone-releasing hormone) analogs, and antibodies.

Wound-healing agents: Exemplary wound-healing agents include the synergistic mixture of enzymes identified in Antarctic hill (*Euphausia superba*). The enzymes of the hill multi-enzyme system are peptide hydrolases, and include both endopeptidases and exopeptidases. See, e.g., Hellgren et al. (1991), *Intl J. Dermatol.* 30(2): 102-103.

Preferred agents for local, topical administration are within the broad classes of compounds known to be topically administrable, including, but not limited to, topical antibiotics and other anti-acne agents, anti-fungal agents, anti-psoriatic agents, antipruritic agents, antihistamines, antineoplastic agents, local anesthetics, anti-inflammatory agents and the like. Suitable topical antibiotic agents include, but are not limited to, antibiotics of the lincomycin family (referring to a class of antibiotic agents originally recovered from *Streptomyces lincolnensis*), antibiotics of the tetracycline family (referring to a class of antibiotic agents originally recovered from *Streptomyces aureofaciens*), and sulfur-based antibiotics, i.e., sulfonamides. Exemplary antibiotics of the lincomycin family include lincomycin itself (6,8-dideoxy-6-[[(1-methyl-4-propyl-2-pyrrolidinyl)-carbonyl] amino]-1-thio-L-threo-α-D-galacto-octopyranoside), clindamycin, the 7-deoxy,7-chloro derivative of lincomycin (i.e., 7-chloro-6,7,8-trideoxy-6-[[(1-methyl-4-propyl-2-pyrrolidinyl)carbonyl]-amino]-1-thio-L-threo-α-D-galacto-octopyranoside), related compounds as described, for example, in U.S. Pat. Nos. 3,475,407, 3,509,127, 3,544,551 and 3,513,155, and pharmacologically acceptable salts and esters thereof. Exemplary antibiotics of the tetracycline family include tetracycline itself, 4-(dimethylamino)-1,4,4α,5,5α,6,11,12α-octahydro-3,6,12,12α-pentahydroxy-6-methyl-1,11-dioxo-2-naphthacene-carboxamide), chlortetracycline, oxytetracycline, tetracycline, demeclocycline, rolitetracycline, methacycline and doxycycline and their pharmaceutically acceptable salts and esters, particularly acid addition salts such as the hydrochloride salt. Exemplary sulfur-based antibiotics include, but are not limited to, the sulfonamides sulfacetamide, sulfabenzamide, sulfadiazine, sulfadoxine, sulfamerazine, sulfamethazine, sulfamethizole, sulfamethoxazole, and pharmacologically acceptable salts and esters thereof, e.g., sulfacetamide sodium. Topical anti-acne agents include keratolytics such as salicylic acid, retinoic acid ("Retin-A"), and organic peroxides, while topical antifungal agents include amphotericin B, benzoic acid, butoconazole, caprylic acid, econazole, fluconazole, itraconazole, ketoconazole, miconazole, nystatin, salicylic acid, and terconazole, and topical antipsoriatic agents include anthralin, azathioprine, calcipotriene, calcitriol, coichicine, cyclosporine, retinoids, and vitamin A The active agent may also be a topical corticosteroid, and may be one of the lower potency corticosteroids such as hydrocortisone, hydrocortisone-2-monoesters (e.g., hydrocortisone-21-acetate, hydrocortisone-21-butyrate, hydrocortisone-2-propionate, hydrocortisone-2-valerate, etc.), hydrocortisone-17, 21-diesters (e.g., hydrocortisone 17,21-diacetate, hydrocortisone-17-acetate-21-butyrate, hydrocortisone-17, 21-dibutyrate, etc.), alclometasone, dexamethasone, flumethasone, prednisolone, or methylprednisolone, or may be a higher potency corticosteroid such as clobetasol propionate, betamethasone benzoate, betamethasone diproprionate, diflorasone diacetate, fluocinonide, mometasone furoate, triamcinolone acetonide, or the like.

Cosmeceutically active agents are also of interest as topical active agents that can be advantageously delivered with the present methods and systems. Cosmeceutically effective active agents include, without limitation, compounds that can reduce the appearance of aging or photodamaged skin, e.g., antioxidants, moisturizers, collagen or hyaluronic acid, and alpha hydroxyacids; skin lightening agents; anti-oxidants such as α-tocopherol and retinol; and sunscreen agents. Other active agents that exert a cosmeceutically beneficial effect and are of particular interest herein are marine biotoxins that cause temporary reduction in muscle activity and can therefore reduce skin wrinkles in the face or elsewhere on the body. Preferred marine biotoxins include the saxitoxins, particularly carbamoyl saxitoxins, sulfamate saxitoxins, and decarbamoyl saxitoxins, with carbamoyl saxitoxin group generally preferred; the latter group includes the gonyautoxins (also referred to as gonytoxins) as well as other compounds having the carbamoyl saxitoxin core. See Hall et al., "The Saxitoxins," in *Marine Toxins, Origin, Structure, and Molecular Pharmacology*, Eds. Hall et al., Ch. 3 (ACS Symposium Series 418, American Chemical Society, Washington D.C. 1990).

In general, the pharmaceutical formulation containing the pharmacologically active agent should be hydrophilic for delivery of a hydrophilic active agent, and hydrophobic, i.e., lipophilic, with lipophilic active agents. To ensure passage of a lipophilic drug through the stratum corneum and into the bloodstream, however, typically requires a mixture of two types of vehicles: a first vehicle that is lipophilic and facilitates passage of the active agent through the stratum corneum; and a second vehicle that is hydrophilic and precludes retention of the active agent just beneath the stratum corneum (which can happen if the agent does not partition well into the lower, more water-rich layers of the skin, particularly the interstitial fluid surrounding the blood vessels). A mixture of lipophilic and hydrophilic vehicles is also advantageous for delivery of a hydrophilic active agent. Suitable hydrophilic vehicles include water, ethanol, isopropanol, water-alcohol mixtures, and the like, while suitable lipophilic vehicles include, but are not limited to, vehicles formulated from the following: phospholipids such as phosphorylated diacyl glycerides, and particularly phospholipids selected from the group consisting of diacyl phosphatidylcholines, diacyl phosphatidylethanolamines, diacyl phosphatidylserines, diacyl phosphatidylinositols, diacyl phosphatidylglycerols, diacyl phosphatidic acids, and mixtures thereof; fatty acids such as isovaleric acid, valeric acid, caproic acid, enanthic acid, caprylic acid, pelargonic acid, capric acid, lauric acid, myristic acid, palmitic acid, stearic acid, arachidic acid, behenic acid, lignoceric acid, oleic acid, linoleic acid, linolenic acid, and arachidonic acid; lower fatty acid esters comprising esters of the foregoing fatty acids, wherein the carboxylic acid group of the fatty acid is replaced with an ester moiety —(CO)—OR wherein R is a $C_1$-$C_3$ alkyl moiety optionally substituted with one or two hydroxyl groups; fatty alcohols corresponding to the aforementioned fatty acids, wherein the carboxylic acid group of the fatty acid is replaced by a —$CH_2OH$ group; glycolipids such as cerebroside and gangliosides; isopropyl myristate; and oils, including animal oils such as cod liver oil and, menhaden oil, and vegetable oils such as babassu oil, castor oil, corn oil, cotton seed oil, linseed oil, mustard oil, olive oil, palm oil, palm kernel oil, peanut oil, poppyseed oil, rapeseed oil, safflower oil, sesame oil, soybean oil, sunflower seed oil, tung oil or wheat germ oil.

The aforementioned vehicles, alone or in combination, can act to enhance the penetration of the active agent into and optionally through the skin, as explained above. In addition or in the alternative, the formulation may contain a compound or composition specifically characterized as a skin penetration enhancer to facilitate passage of a pharmacologically active agent into and through the skin, as the stratum corneum, i.e., the outermost layer of the skin, can, for some agents, provide a significant barrier. A penetration enhancer should, like the other components of the transdermal system, minimize the possibility of skin damage, irritation, sensitivity, and systemic toxicity. Examples of suitable penetration enhancers include, but are not limited to, ethers such as diethylene glycol monoethyl ether (available commercially as Transcutol®) and diethylene glycol monomethyl ether; surfactants such as sodium laurate, sodium lauryl sulfate, cetyltrimethyl-ammonium bromide, benzalkonium chloride, poloxamers (e.g., Pluronic 231, 182, 184), polysorbates (e.g., Tween 20, 40, 60, 80) and lecithin; alcohols such as ethanol, propanol, octanol, benzyl alcohol, and the like; polyethylene glycol and esters thereof such as polyethylene glycol monolaurate (PEGML; see, e.g., U.S. Pat. No. 4,568,343); amides and other nitrogenous compounds such as urea, dimethylacetamide (DMA), dimethylformamide (DMF), 2-pyrrolidone, 1-methyl-2-pyrrolidone, ethanolamine, diethanolamine and triethanolamine; terpenes; alkanones; and organic acids, particularly citric acid and succinic acid. Azone® and sulfoxides such as DMSO and $C_{10}MSO$ may also be used, but are less preferred.

The pharmaceutical formulation can also include one or more conventional additives such as opacifiers, antioxidants, thickening agents, stabilizers, surfactants, preservatives, and the like. In addition, the pharmaceutical formulation, like the SCA layer, may contain an irritation-mitigating additive such as glycerin to minimize or eliminate the possibility of skin irritation or skin damage that might result from a particular active agent or other component of the system.

While the pharmaceutical formulation is loaded into the porous drug reservoir, an additional formulation can be incorporated into one or more other layers of the system. For instance, a second pharmaceutical formulation can be loaded into a second drug reservoir in the lower module, or into a layer within the upper module, such as the PSA layer or another layer that may be present. As another example, as alluded to previously, a formulation containing an activator compound can be loaded into a layer of the system that is above the drug reservoir, such that following assembly of the system and placement on the skin, the activator compound will permeate down through the system, activating a drug precursor present in the drug reservoir.

It will also be understood that various solvents, compounds and compositions can be incorporated into the active agent formulation and/or into different layers of the transdermal system in order to modulate solubility, driving force, and flux through and out of the system, all of which are interrelated parameters.

IV. Assembly, Drug Loading, and Use

In one embodiment, the transdermal delivery system is assembled as follows: A pharmaceutical formulation containing the pharmacologically active agent to be delivered is loaded into the porous drug reservoir of the lower module. This can be done in any number of ways, e.g., by pipetting, pouring, and/or spreading the formulation onto the exposed surface of the reservoir (i.e., the upper surface of the lower module), by injection into the reservoir, by immersion of the reservoir into a container housing the formulation, or the like. After drug loading is complete, the first release liner is peeled away from the basal surface of the upper module, the edges of the upper and lower modules are aligned with the basal surface of the upper module facing the upper surface of the lower module, and the upper module is lightly pressed into place on the lower module. As the PSA layer of the upper module directly contacts the upper surface of the lower module, the modules remain affixed to each other. Immediately prior to use, the second release liner is removed from the basal surface of the lower module, and the assembled transdermal system is pressed onto the selected location on an individual's skin. Drug release from the device begins shortly thereafter.

The invention accordingly encompasses a method for transdermally administering a pharmacologically active agent to a subject, where the method involves applying to the skin of the subject the modular transdermal delivery system as just provided, i.e., a transdermal system that comprises: an upper module comprising an outer backing layer and a pressure-sensitive adhesive layer laminated thereto; and, affixed to the pressure-sensitive adhesive layer, a lower module comprising a porous drug reservoir that is adhered to the pressure-sensitive adhesive layer, a skin contact adhesive underlying the drug reservoir layer that serves as the basal surface of the system in contact with the skin during drug delivery, and, contained within the porous drug reservoir layer, a pharmaceutical formulation containing a pharmacologically active agent or precursor thereto.

It is to be understood that while the invention has been described in conjunction with a number of specific embodiments, the foregoing description as well as the examples that follow are intended to illustrate and not limit the scope of the invention. Other aspects, advantages and modifications will be apparent to those skilled in the art. All patents, patent applications, and publications mentioned here are hereby incorporated by reference in their entireties.

EXPERIMENTAL

Example 1: Manufacture of the Modular Transdermal System

A coating bar is used with a selected gap height, e.g., 4 mils, 10 mils, 16 mils, etc. These are illustrative dimensions and not intended to be limiting.

Upper module: A letter-sized backing film of choice is taped to a glass plate for easier handling. The desired adhesive solution is poured at the one end of the backing film. A coating bar of given gap height is used to evenly spread the adhesive solution over the backing material. The coated backing is placed into a vacuum oven overnight for removal of all solvents. Should one of the compounds loaded into the adhesive also evaporate, vacuum and temperature have to be adjusted accordingly. An overage in the casting solution can be used to ensure the desired degree of compound loading in the dry adhesive. When the adhesive is dry and/or cured, a releaser liner is laminated to the adhesive. The laminate is stored for future usage. Note: for the upper module, the coating can also be started on the release liner and then the backing is applied.

Lower module: A letter-sized release liner film of choice is taped to a glass plate for easier handling. The desired adhesive solution is poured at the one end of the releaser liner film. A coating bar of given gap height is used to even spread the adhesive solution over the backing material. The coated release liner is placed into a vacuum oven overnight for removal of all solvents. Should one of the compounds loaded into the adhesive also evaporate, vacuum and temperature have to be adjusted accordingly. An overage in the casting solution can be used to result in the desired compound loading in the dry adhesive. When the adhesive is dry and/or cured the microporous film is laminated to the adhesive. The laminate is stored for future usage.

Manufacture of a Round 20-Cm$^2$ Transdermal Delivery System:

A round punch of 5.2 cm in diameter is used to punch out a round laminate disk out of the upper module laminate made as described above. The upper disc is slightly larger than 20 cm$^2$. A round punch of 5.04 cm diameter is used to punch out a round laminate disk out of the lower module laminate made as described above.

The selected microporous reservoir (MPR) of the lower module laminate is 200 μm thick and has a porosity of 50%, i.e. it can hold a maximum of 100 μl/cm$^2$ of active agent formulation without overflowing. To the MPR, 20×95 μl=1.9 ml of formula are added. Then, the release liner of the upper module is slowly removed, exposing ⅛ of the adhesive layer. The partially removed release liner is bent back and folded to allow alignment of the exposed adhesive with the lower part of the patch. When the exposed adhesive is firmly adhered to the lower part, the part of the upper patch that is not adhered is bent up slightly to allow the user to grab the bent-back release liner section and continue pulling the release liner off, so that the whole upper module can be attached to the lower module.

Figure 2:
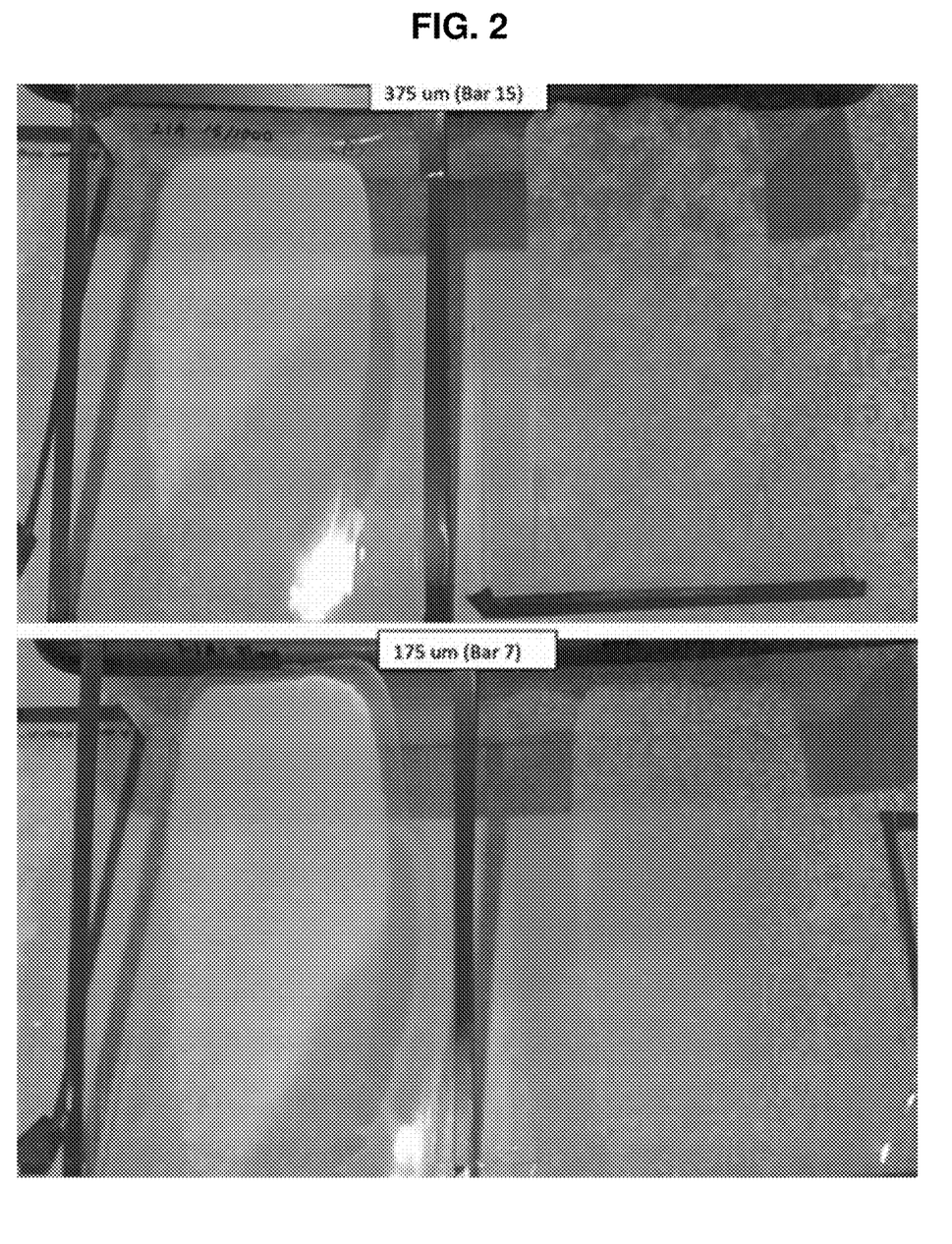
FIG. 2 are photographs showing dried films prepared using the method of Example 1.

The final dried films are shown in the photographs of FIG. 2.

Example 2: MPR and MPR/Adhesive Permeation Screening

Figure 3:
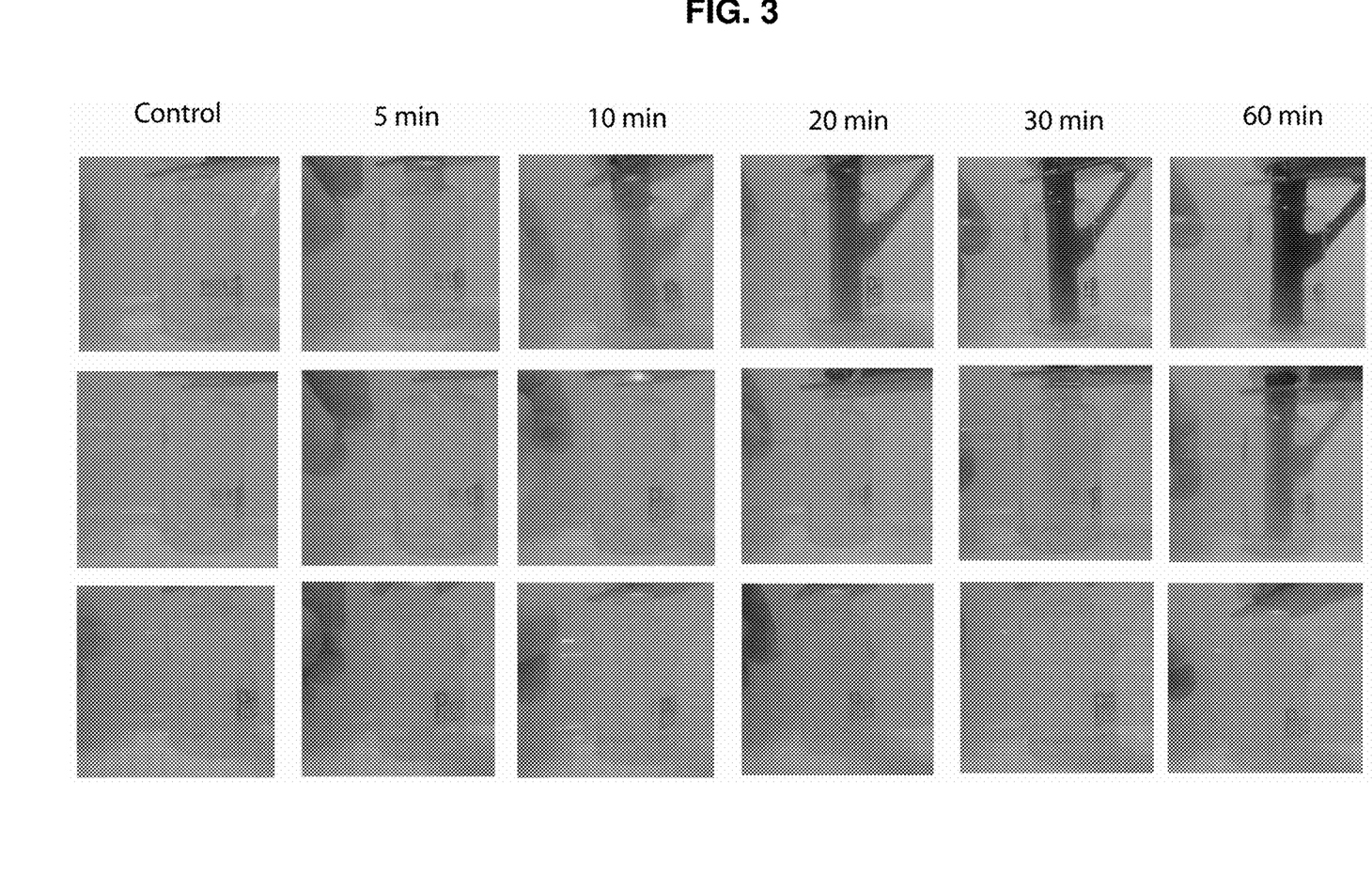
FIG. 3 illustrates the results obtained for microporous reservoir (MPR) and MPR/adhesive permeation screening, as described in Example 2.

To estimate different lower module permeation characteristics, a visual test was derived using Franz cells. Methylene blue and other water or lipid-soluble colorants in the 300 Da range were added to the delivery formulation and visually assessed for the ability to deliver and control active permeation. Results are illustrated in FIG. 3, which shows three different barriers, with the upper module fastest and the lower module slowest. Following this preliminary screening, additional tests with pig and cadaver skin can be used in conjunction with HPLC analysis to determine the skin flux obtained with different lower modules.

Example 3: Large-Scale, Commercial Manufacture of Parts

Typical and standard processes may be used, for example knife over roll coating, drying of adhesive in oven, with or without in-line cutting.

Without cutting, the laminate is rolled up and provided to the converter to cut out the form and shape and size to their specifications.

The invention claimed is:

1. A method for transdermally administering a pharmacologically active agent to a subject, the method comprising:
   (a) applying a separable, modular transdermal drug delivery system containing a pharmaceutical formulation comprising a first effective amount of the active agent to the skin of the subject and allowing the delivery system to remain affixed to the skin and deliver a total intended dose of the active agent to the subject throughout a first drug delivery period, wherein the transdermal drug delivery system is comprised of an upper module and a lower module that adheres to the skin and contains a porous drug reservoir that houses the pharmaceutical formulation, and, after completion of the drug delivery period:
   (b) separating the upper module from the porous drug reservoir layer-containing lower module, and then carrying out a further step selected from:
   (c) refilling the porous drug reservoir with the pharmaceutical formulation and recombining the lower module with the upper module to deliver the total intended dose of the active agent to the subject throughout a second drug delivery period;
   (d) refilling the porous drug reservoir layer with a pharmaceutical formulation comprising second effective amount of the active agent different from the first effective amount, and recombining the lower module with the upper module to form a dose-modified transdermal drug delivery system and deliver a different total intended dose of the active agent to the subject throughout a second drug delivery period;
   (e) refilling the porous drug reservoir layer with a pharmaceutical formulation comprising an effective amount of a different pharmacologically active agent, and recombining the lower module with the upper module to deliver a total intended dose of the different active agent to the subject throughout a second drug delivery period; and
   (f) refilling the drug delivery system with a pharmaceutical formulation comprising an effective amount of the active agent and at least one different active agent, and recombining the lower module with the upper module to deliver a total intended dose of the active agent and the least one different active agent to the subject throughout a second drug delivery period;
   wherein step (b) and the further step selected from (c), (d), (e), and (f) are performed by a post-manufacture medical practitioner or by the subject.

2. The improved method of claim 1, wherein step (b) and the further step selected from (c), (d), (e), and (f) are performed by a post-manufacture medical practitioner.

3. The improved method of claim 1, wherein step (b) and the further step selected from (c), (d), (e), and (f) are performed by the subject.

4. The method of claim 1, wherein the pharmacologically active agent is selected from: analgesic agents; anesthetic agents; antiarthritic agents; respiratory drugs; anticancer agents; anticholinergics; anticonvulsants; antidepressants; antidiabetic agents; antidiarrheals; antihelminthics; antihistamines; antihyperlipidemic agents; antihypertensive agents; anti-infective agents; anti-inflammatory agents; antimigraine preparations; antinauseants; antineoplastic agents; antiparkinsonism drugs; antipruritics; antipsychotics; antipyretics; antispasmodics; antitubercular agents; antiulcer agents; antiviral agents; anxiolytics; appetite suppressants; attention deficit disorder drugs; cardiovascular preparations; beta-blockers; antiarrhythmic agents; central nervous system stimulants; cough and cold preparations; diuretics; genetic materials; herbal remedies; hormonolytics; hypnotics; hypoglycemic agents; immunosuppressive agents; leukotriene inhibitors; mitotic inhibitors; muscle relaxants; narcotic antagonists; nicotine; nutritional agents; ophthalmic drugs; parasympatholytics; peptide drugs; psychostimulants; sedatives; steroids; sympathomimetics; tranquilizers; vasodilators; wound-healing agents; and combinations of any of the foregoing.

5. The method of claim 4, wherein the pharmacologically active agent is selected from analgesic agents and combinations thereof.

6. The method of claim 1, wherein the improvement further comprises employing a cannabinoid as the pharmacologically active agent.

7. The method of claim 6, wherein the cannabinoid is selected from tetrahydrocannabinol (THC), dronabinol, cannabichromanone, cannabichromene (CBC), cannabichromenic acid, cannabichromevarin (CBCV), cannabichromevarinic acid, cannabicitran (CBT), cannabicoumaronone (CBCON), cannabicyclol (CBL), cannabicyclolic acid, cannabicyclovarin, cannabidiol (CBD), cannabidiol monomethyl ether, dimethyl heptylpentyl cannabidiol (DMHP-CBD), cannabidiolic acid, cannabidiorcol, cannabidivarin (CBV), cannabidivarinic acid, cannabielsoin (CBE), cannabielsoinic acid, cannabifuran, cannabigerol (CBG), cannabigerol monomethyl ether (CBGM), cannabigerolic acid, cannabigerolic acid monomethyl ether, cannabigerovarin (CBGV), cannabigerovarinic acid, cannabiglendol, cannabinodiol, cannabinodivarin, cannabinol (CBN), cannabinolic acid, cannabinol methyl ether, cannabiorcol, cannabiripsol, cannabitetrol, cannabitriol, 10-O-ethyl-cannabitriol, cannabivarichromene, cannabivarin, dehydrocannabifuran, 1,2-dihydroxyhexahydrocannabinol, 1,2-dihydroxyhexahydrocannabinol acetate, dimethylheptylpyran, isotetrahydrocannabivarin, levonantradol, nabilone, rimonabant, 9-tetrahydrocannabinolic acid, 9-tetrahydrocannabiorcol, 9-tetrahydrocannabiorcolic acid, 9-tetrahydrocannabivarin, 9-tetrahydrocannabivarinic acid, 8,11-dihydroxy-9-tetrahydrocannabinol, 8,9-dihydroxy-6a,10a-tetrahydrocannabinol, 8-tetrahydrocannabinol, 8-isotetrahydrocannabinol, 8-tetrahydrocannabinolic acid, 10-oxo-6a,10a-tetrahydrocannabinol (OTHC), HU-210 (1,1-dimethylheptyl-11-hydroxy-8-THC), HU-331 (3-hydroxy-2-[(1R)-6-isopropenyl-3-methyl-cyclohex-2-en-1-yl]-5-pentyl-1,4-benzoquinone), JWH-018 (1-pentyl-3-(1-naphthoyl)indole), JWH-073, AM-2201 (1-(5-fluoropentyl)-3-(1-naphthoyl)indole), and CP-55,940 (2-((1S,2S,5S)-5-hydroxy-2-(3-hydroxypropyl) cyclohexyl)-5-(2-methyloctan-2-yl)phenol).

8. The method of claim 7, wherein the pharmacologically active agent comprises cannabidiol.

9. The method of claim 8, wherein the pharmaceutical formulation further includes a terpenoid.

10. The method of claim 1, wherein the pharmaceutical formulation comprises a precursor to the pharmacologically active agent which is converted to its active form during drug delivery.

11. The method of claim 1, wherein:
the upper module comprises an outer backing layer and a pressure-sensitive (PSA) layer laminated thereto; and
the lower module comprises the porous drug reservoir layer, the porous drug reservoir layer being capable of adhering to the PSA layer of the upper module, and a skin-contact adhesive affixed to the drug reservoir layer.

12. The method of claim 11, wherein the skin-contact adhesive comprises a skin-contact adhesive layer that is laminated to the drug reservoir layer and serves as the basal surface of the system that adheres to the skin during use.

13. The method of claim 11, wherein the, skin-contact adhesive comprises a peripheral ring underlying the drug reservoir layer.

14. The method of claim 11, wherein recombining the lower module with the upper module comprises contacting the PSA layer of the upper module with the drug reservoir layer of the active-agent loaded lower module.

15. The method of claim 11, wherein the PSA layer comprises a permeation enhancer.

16. The method of claim 1, wherein the porous drug reservoir layer has a porosity gradient such that porosity gradually decreases from an uppermost region of the reservoir layer to a lowermost region of the reservoir layer.

17. The method of claim 1, further comprising:
removing the transdermal drug delivery system from the subject's skin after step (a) and prior to step (b); and
during steps (c), (d), (e), or (f), reapplying the transdermal drug delivery system to the skin of the subject after recombining the lower module with the upper module.

18. A method for transdermally administering a pharmacologically active agent to a subject, the method comprising:
(a) applying a separable, modular transdermal drug delivery system containing a pharmaceutical formulation comprising a first effective amount of the active agent to the skin of the subject and allowing the delivery system to remain affixed to the skin and deliver a total intended dose of the active agent to the subject throughout a first drug delivery period, wherein the transdermal drug delivery system is comprised of an upper module and a lower module that adheres to the skin and contains a porous drug reservoir that houses the pharmaceutical formulation, and, after completion of the drug delivery period:
(b) separating the upper module from the porous drug reservoir layer-containing lower module;
(c) refilling the porous drug reservoir with the pharmaceutical formulation; and
(d) recombining the lower module with the upper module to deliver the total intended dose of the active agent to the subject throughout a second drug delivery period.

19. A method for transdermally administering a pharmacologically active agent to a subject, the method comprising:
(a) applying a separable, modular transdermal drug delivery system containing a pharmaceutical formulation comprising a first effective amount of the active agent to the skin of the subject and allowing the delivery system to remain affixed to the skin and deliver a first total intended dose of the active agent to the subject throughout a first drug delivery period, wherein the transdermal drug delivery system is comprised of an upper module and a lower module that adheres to the skin and contains a porous drug reservoir that houses the pharmaceutical formulation, and, after completion of the drug delivery period:
(b) separating the upper module from the porous drug reservoir layer-containing lower module;
(c) refilling the porous drug reservoir with a second pharmaceutical formulation comprising a second effective amount of the active agent different from the first effective amount; and (d) recombining the lower module with the upper module to deliver a second total intended dose of the active agent to the subject throughout a second drug delivery time period, wherein the second total intended dose is different from the first total intended dose.

20. A method for transdermally administering a pharmacologically active agent to a subject, comprising:
(a) applying a separable, modular transdermal drug delivery system containing a pharmaceutical formulation comprising a first effective amount of the active agent to the skin of the subject and allowing the delivery system to remain affixed to the skin and deliver a total intended dose of the active agent to the subject throughout a first drug delivery period, wherein the transdermal drug delivery system is comprised of an upper module and a lower module that adheres to the skin and contains a porous drug reservoir that houses the pharmaceutical formulation, and, after completion of the drug delivery period:
(b) separating the upper module from the porous drug reservoir layer-containing lower module;
(c) refilling the porous drug reservoir with a second pharmaceutical formulation comprising an effective amount of a second pharmacologically active agent different from the first active agent; and
(d) recombining the lower module with the upper module to deliver a total intended dose of the second active agent to the subject throughout a second drug delivery time period.

21. A method for transdermally administering a pharmacologically active agent to a subject, comprising:
(a) applying a separable, modular transdermal drug delivery system containing a pharmaceutical formulation comprising a first effective amount of the active agent to the skin of the subject and allowing the delivery system to remain affixed to the skin and deliver a total intended dose of the active agent to the subject throughout a first drug delivery period, wherein the transdermal drug delivery system is comprised of an upper module and a lower module that adheres to the skin and contains a porous drug reservoir that houses the pharmaceutical formulation, and, after completion of the drug delivery period:
(b) separating the upper module from the porous drug reservoir layer-containing lower module;
(c) refilling the drug delivery system with a second pharmaceutical formulation comprising the first active agent and at least one additional active agent;
(e) recombining the lower module with the upper module to deliver a total intended dose of both the first active agent and the at least one additional active agent to the subject throughout a second drug delivery time period.

22. A method for transdermally administering a cannabinoid analgesic agent to a subject, the method comprising:
(a) applying a separable, modular transdermal drug delivery system containing a pharmaceutical formulation comprising a first effective amount of the cannabinoid analgesic agent to the skin of the subject and allowing the delivery system to remain affixed to the skin to deliver a total intended dose of the cannabinoid analgesic agent to the subject throughout a first drug delivery time period;
(b) separating the upper module of the delivery system from the porous drug reservoir layer-containing lower module, and then carrying out a further step selected from:
(c) refilling the porous drug reservoir with the pharmaceutical formulation and recombining the lower module with the upper module to re-form the drug delivery system and deliver the total intended dose of the cannabinoid analgesic agent to the subject throughout a second drug delivery time period;
(d) refilling the porous drug reservoir with a pharmaceutical formulation comprising a different effective amount of the cannabinoid analgesic agent, and combining the lower module with the upper module to form a dose-modified transdermal drug delivery system and deliver a different total intended dose of the cannabinoid analgesic agent to the subject throughout a second drug delivery time period; and
(e) refilling the porous drug reservoir with a pharmaceutical formulation comprising an effective amount of the cannabinoid analgesic agent and at least one different active agent, and combining the lower module with the upper module to deliver the cannabinoid analgesic agent and the at least one additional active agent to the subject throughout a second drug delivery time period,
wherein step (b) and the further step selected from (c), (d), and (e) are performed by a post-manufacture medical practitioner or by the subject.

23. The method of claim 22, wherein the cannabinoid analgesic agent comprises cannabidiol.

24. The method of claim 23, wherein the pharmaceutical formulation of step (a) further includes a terpenoid.

* * * * *